United States Patent [19]

Bayless et al.

[11] Patent Number: 4,927,850

[45] Date of Patent: May 22, 1990

[54] ANTIOXIDANT COMPOSITIONS AND METHODS FOR AMELIORATING INFLAMMATORY SYMPTOMS OF RESPIRATORY DISEASE

[76] Inventors: Robert K. Bayless, 6509 Pevensey Dr., Austin, Tex. 78745; Gerald P. Hirsch, 8414 Hanbridge La., Austin, Tex. 78736

[21] Appl. No.: 179,230

[22] Filed: Apr. 8, 1988

[51] Int. Cl.$^5$ .................... A61K 31/20; A61K 31/34; A61K 31/195; A61K 31/355

[52] U.S. Cl. ................................. 514/458; 514/474; 514/494; 514/559; 514/562

[58] Field of Search ............... 514/562, 458, 494, 559, 514/474

[56] References Cited

U.S. PATENT DOCUMENTS

| | | | |
|---|---|---|---|
| 2,457,820 | 1/1949 | Howe et al. | 514/562 |
| 3,773,930 | 11/1973 | Mohammed et al. | 514/60 |
| 4,315,028 | 2/1982 | Scheinberg | 424/290 |
| 4,409,233 | 10/1983 | Tsukada et al. | 514/562 |
| 4,424,216 | 1/1984 | Ceraml et al. | 424/128 |
| 4,499,076 | 2/1985 | Ohashi et al. | 514/54 |
| 4,649,040 | 3/1987 | Pitha | 514/562 |
| 4,711,780 | 12/1987 | Fahim | 514/562 |

FOREIGN PATENT DOCUMENTS

| | | | |
|---|---|---|---|
| 2618099 | 11/1977 | Fed. Rep. of Germany | 514/562 |
| 003667M | 11/1965 | France | 424/319 |

OTHER PUBLICATIONS

*Facts and Comparisons*, pp. 54–55 (1983).
Le Fur, Chem. Abst. 99: 146145s, 1983.
*Physicians' Desk Reference*, 31st Ed (1977), pp. 1127–1134.
Garrison, *Lysine, Tryptophan, and Other Amino Acids*, pp. 14–17 (1982).
Smolin et al., "The Use of Betaine for the Treatment of Homocystinuria", Jour. Ped., vol. 99, No. 3, pp. 467–472.
See Attached Schedule A.
Ames; *Science*, "Dietary Carcinogens and Anticarcinogens", vol. 221, No. 4617, Sep. 23, 1983, pp. 1256–1264.
Tsan and Chen, *J. Clin. Invest.*, "Oxidation of Methionine by Human Polymorphonuclear Leukocytes", vol. 65, May 1980, pp. 1041–1050.
Stegink et al.; *Journal of Nutrition*, "Effects of Equimolar Doses of L-Methionine, D-Methionine and L--Methionine-dl-Sulfoxide on Plasma and Urinary Amino Acid Levels in Normal Adult Humans", vol. 116, 1986, pp. 1185–1192.
Finkelstein and Martin; *The Journal of Biological Chemistry*, "Methionine Metabolism in Mammals", vol. 261, No. 4, Feb. 1986, pp. 1582–1587.
Cho et al.; *Journal of Parenteral and Enteral Nutrition*, "D-Methionine Utilization in Young Miniature Pigs, Adult Rabbits, and Adult Dogs", vol. 4, No. 6, pp. 544–547.
Stegink et al.; *Journal of Nutrition*, "Plasma Methionine Levels in Normal Adult Subjects After Oral Loading with 1-Methionine and N-Acetyl-1-Methionine", 1980, pp. 42–49.
Rotruck and Boggs; *Journal of Nutrition*, "Comparative Metabolism of L-Methionine and N-Acetylated Derivatives of Methionine", 1975, 105: pp. 331–337.
*The Merck Index Tenth, Edition;* "Methionine", 1983, p. 5849.
Cuperus et al.; *Arthritis and Rheumatism*, "Antiarthritic Drugs Containing Thiol Groups Scavenge Hypochlorite and Inhibit Its Formation by Myeloperoxidase From Human Leukocytes", vol. 28, No. 11, Nov. 1985, pp. 1228–1233.

*Primary Examiner*—Stanley J. Friedman
*Attorney, Agent, or Firm*—J. F. Long

[57] ABSTRACT

This invention concerns novel dietary or therapeutic antioxidant compositions containing as the active agent the amino acid methionine, and/or one or more related compounds including certain metabolic precursor compounds, and novel methods employing the compositions for inhibiting inflammatory symptoms of respiratory disease. The compounds include the methionine hydroxy analog, the S-methyl methionine analog, and methionine compounds having the structural formula I

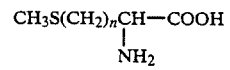

$$CH_3S(CH_2)_nCH-COOH \atop | \atop NH_2 \qquad I$$

dl- or d- form and pharmaceutically acceptable N- (mono- and dicarboxylic acid) acyl derivatives and alkyl esters thereof, where n is an integer from 1 to 3.

10 Claims, No Drawings

ANTIOXIDANT COMPOSITIONS AND METHODS FOR AMELIORATING INFLAMMATORY SYMPTOMS OF RESPIRATORY DISEASE

TECHNICAL FIELD

This invention concerns novel dietary and therapeutic antioxidant compositions containing as an active agent the amino acid methionine (also known as "Met"), and/or one or more related compounds including certain metabolic precursor compounds. The invention also concerns novel methods employing the compositions for ameliorating or alleviating inflammatory symptoms of respiratory disease in a subject.

BACKGROUND OF THE INVENTION

A variety of efforts have been made over many years to elucidate the mechanisms and origins of the various forms of environmental risk factors thought to contribute to inflammatory symptoms of respiratory disease, especially in the case of smoke and toxic materials that are inhaled, e.g. air-borne asbestos particles.

Many substances that are risk factors have been identified in smoke. The urine of smokers has been shown to contain substances that are mutagenic for replicating bacteria.

Tobacco smoke contains other materials that may contribute to symptoms of respiratory disease. For example, in the blood nicotine has been shown to attract immunocytes (white cells) known as neutrophils; these can contribute to respiratory cell damage. Symptoms of respiratory disease include chronic coughing, increased cough frequency, impaired lung function and capacity, abnormal mucous production, and the like. For a review of life-style risk factors and of protective factors in the diet, see the article by Bruce N. Ames entitled "Dietary Carcinogens and Anticarcinogens", Science, 221: 1256-1263, 1983, incorporated herewith by reference.

Methionine has been shown to be a target for the products of stimulated polymorphonuclear neutrophils (PMNs) (Tsan and Chen, J. Clin. Invest., 65:1041-1050, 1980). The granular fraction of PMNs oxidizes methionine to its sulfoxide in the presence of peroxide. Peroxide does not oxidize methionine to its sulfoxide at normal physiological concentrations.

Some of the differences measured in the relative effectiveness of methionine compounds and other chemicals, especially antioxidants, can be attributed to the control mechanisms that operate in animals and man to regulate the amounts of these substances wherein giving more of a substance does not significantly increase blood and tissue levels of that substance. Stegink, J. Nutrition, 116: 1185-1192, 1986, showed that 0.5 gm of methionine elevated total blood methionine 2-fold for 2 hours with l-methionine but 3-fold for 4 hours with d-methionine.

Elevated methionine levels can affect concentration of other metabolites. Increasing dietary methionine 3-fold above normal values in rats causes a decrease in serine and betaine in the liver (Finkelstein and Martin, J. Biol. Chem. 261: 1582-1587, 1986).

Regarding human nutrition, l-methionine is an essential amino acid (The Merck Index, IX, 5840, 1976), whereas d-methionine is not essential. Stegink, supra, shows that adult humans do not utilize d-methionine efficiently as a methionine source. For purposes of metabolism, l-methionine via S-adenosylmethiomine has an important methylating function. In this function it loses a methyl group from its sulfur atom to become homocysteine. Homocysteine, as is known, when in excess can lead to homocysteinuria and may be disease associated.

Cuperus, Arthritis and Rheumatism, 28: 1228-1233, 1985, describes a feature of inflamed synovial fluid, such as that occurring in arthritis patients, as the accumulation of polymorphonuclear (PMN) leukocytes. The function of the leukocytes as has been alluded to, is the destruction of invading elements such as micro-organisms. For this destruction, the leukocyte releases hydrogen peroxide and enzymes, e.g., myeloperoxidase, into the extracellular fluid. In the presence of hydrogen peroxide and chloride ion, myeloperoxidase catalyzes the formation of reactive hypochlorous acid (HOCl) which can oxidize tissue components and plasma protease inhibitors. Oxidation and subsequent inactivation of these protease inhibitors in vivo may lead to unrestrained proteolysis, resulting in severe tissue damage.

dl-Methionine is available as a one-a-day food supplement in 500-mg. oral tablet form. The normal serum level of methionine in man is 15 ppm.

U.S. Pat. No. 3,952,115 describes foodstuffs containing N-acyl l-methionine esters and N-acyl l-cysteine esters.

In view of the widespread incidence of inflammatory symptoms of respiratory disease, a need exists for means of preventing or ameliorating the symptoms and serious consequences of the disease.

It is therefore an object of the present invention to provide compositions for the alleviation and treatment of inflammatory respiratory disease conditions of man and animals.

It is also an object of the invention to provide means for the prevention, inhibition and treatment of disease conditions of the kind described.

It is a further object of the invention to provide means for preventing or alleviating symptoms of homocysteinuria that may result from excess methionine intake.

These and other objects, features and advantages will be seen from the following detailed description of the invention.

SUMMARY AND DETAILED DESCRIPTION OF THE INVENTION

Our invention is based on the discovery that certain methionine or methionine-type compounds in the dl-form or d-form at relatively high, well-tolerated doses are utilized well and due to the presence of the d-form, are potent antioxidant and antiinflammatory agents in man and animals. The invention includes means for inhibiting or treating conditions presented as an inflammatory response of respiratory disease.

For purposes of the invention, one uses in the dl-or d-form at least one methionine-type compound selected from the methionine hydroxy analog, the S-methyl methionine analog, and methionine compounds having the structural formula I:

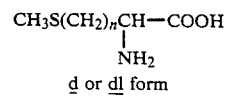

$$CH_3S(CH_2)_nCH-COOH \atop | \atop NH_2$$

I d or dl form and pharmaceutically acceptable N- (mono- and dicarboxylic acid) acyl derivatives and alkyl esters thereof, where n is an integer from 1 to 3.

Thus, the methionine-type compound (for convenience sometimes referred to herein as "methionine" or "methionine compound") may be normethionine (n=1), methionine (n=2), homoethionine (n=3), the hydroxy analog, the S-methyl methionine analog (also known as vitamin U) or the acyl or alkyl ester derivative thereof. Exemplary acyl derivatives are the formyl, acetyl, propionyl, and succinyl derivatives, of which the formamide, acetamide and succinyl derivatives are preferred. Exemplary ester derivatives are the methyl, ethyl and isopropyl esters.

In one method aspect, the invention concerns a method for ameliorating inflammatory symptoms of respiratory disease in a subject. The method comprises administering to the subject an antioxidant in dosage form preferably an oral dosage form, comprising an effective antiinflammatory amount of at least one methionine compound as defined above. In a preferred embodiment, the dosage form contains at least one methionine compound as defined, which serves as an effective antioxidant as described, and at least one added dietary antioxidant in an antioxidant effective amount. Preferred antioxidants are vitamins A, C and E, beta carotene, selenium, zinc and glutathione, each preferably in recommended daily allowance (RDA). By using agents different in mechanism of action and agents having similar mechanisms of action, a synergistic antioxidant effect can be expected.

The method in a preferred embodiment comprises administering in the dosage form with the methionine content at least one homocysteine reducing or remethylating compound sometimes referred to herein as a homocysteine affecting compound. The homocysteine affecting compound is at least one amino acid or nutrient selected from betaine, glycine, serine, vitamin B12, vitamin B6, and folic acid or folate, the compound being present in an amount sufficient to enable the systemic conversion of homocysteine to methionine or cysteine. The metabolic pathways for such conversion are detailed in Lehninger's Biochemistry, 2nd Ed., Chapter 25, Worth Publishers, Inc., 1978, incorporated herewith by reference.

Background for this is that methionine may have an adverse effect when given to subjects with vitamin B12 or folate deficiency. This effect is thought to be due to a buildup of systemic homocysteine; homocysteine is poorly remethylated in the absence or deficiency of vitamin B12 or folate. Also, the vitamin B6 level may be too low for the metabolism of homocysteine to cysteine by way of cystathionine. Thus, chronic consumption of excess l-methionine, for example, may result in mild homocysteine elevation unless other co-factor substances are used or supplemented to stimulate the transformation of the excess homocysteine. The buildup is avoided, according to the invention, by including at least one homocysteine affecting compound in the dosage: betaine in an amount such that homocysteine is remethylated to methionine; glycine or serine to insure that homocysteine can be reduced by way of cystathionine to cysteine; vitamin B12 and/or folate to insure that homocysteine can be systemically remethylated; and vitamin B6 to insure that homocysteine can be metabolized to cysteine. The amino acids betaine, glycine and serine preferably are each present in the dosage in an amount from 1/10 to 10 times the amount of the methionine compound, preferably betaine and preferably an equal amount of betaine. The nutrients vitamins B12, B6 and folate preferably are each present in the recommended daily allowance (RDA).

For ameliorating the inflammatory symptoms in a preferred embodiment, the methionine compound is administered in a daily dosage, preferably oral or parenteral, in the range from 10 to 100 mg/kg of body weight until the inflammation is relieved. A preferred treatment regimen in man is a daily dose, preferably oral, of at least 20 to 30 mg/kg of body weight taken in even spaced doses of the methionine compound or in a single equivalent sustained release dosage form or controlled release dosage form, preferably as dl-methionine. A preferred application is in a method for improving lung function or decreasing the frequency of disease-related chronic coughing in a subject where the dosage regimen preferably daily is sufficient in magnitude and duration, to improve said function (e.g. improvement in expelled air volume) or to decrease said frequency.

The mechanism underlying the present invention is believed to be that the methionine compound acts in vivo to inhibit the release by polymorphonuclear leukocytes of hypochlorous acid and other oxidants so that systemic oxidation, proteolysis, and tissue damage are inhibited. It is believed that the l-form of the methionine compound serves to fulfill its essential, recognized nutritional need whereas it is the d-form that has a previously unrecognized potent and different action at high dosage which is a well tolerated antiinflammatory activity.

In a composition aspect, the invention concerns a dietary or therapeutic antioxidant composition preferably in dosage form, containing an antiinflammatorily effective amount of at least one methionine compound as defined above, and at least one homocysteine affecting compound as defined above in an amount sufficient to enable the systemic conversion of homocysteine to methionine or cysteine.

Another preferred dietary or therapeutic composition is one, preferably in oral ingestible form, containing at least one methionine compound as defined above and in the amount specified, and at least one added dietary antioxidant as defined, in an antioxidant effective amount, preferably a recommended daily allowed amount.

PREPARATION OF PHARMACEUTICAL AND DIETARY COMPOSITIONS

The compositions of the invention can be prepared and administered in a wide variety of dosage forms. It will be clear to those skilled in the art that the following dosage forms may comprise as the active component, the methionine compound as defined above, a corresponding pharmaceutically acceptable salt, or a mixture thereof.

For preparing pharmaceutical compositions from the methionine compounds pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. The active compound is mixed with carrier having the necessary binding properties in suitable proportions and compacted in the shape and size desired. The powders and tablets preferably contain the preferred amounts of the active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted in suitable amount, e.g., from 100 mg to 1,000 mg according to the particular application and the potency of the active ingredient.

In therapeutic use as pharmacological agents the methionine compound or compounds utilized in the pharmaceutical method of this invention are administered at the initial daily dosage of about 10 to about 100 mg per kilogram. A dose of about 20 to 30 mg per kilogram is preferred. The dosages, however, may be varied depending upon the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The daily dosage preferably is in a single sustained release dosage form or controlled release form (e.g. an enteric coated or slow release dosage form) to insure that the dosage is released in the intestine or that a uniformly elevated blood level of the methionine compound is achieved.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

Unit dosage forms used herein refer to physically discrete units suitable as unitary dosages for the subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in subjects having a diseased condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. In the case of compositions containing supplementary active ingredients, the dosages are determined by reference to the usual dose and the manner of administration of the said ingredients.

The invention and the best mode of practicing the same as illustrated by the following examples of preferred embodiments.

EXAMPLE 1

| CAPSULES Example 1a d-Methionine 100 mg, 250 mg or 500 mg | |
|---|---|
| d-Methionine | 500 g |
| Lactose USP, Anhydrous q.s. or | 200 g |
| Sterotex Powder HM | 5 g |

Combine the methionine and the Lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg. 352.5 mg or 705 mg of the blend, respectively, for the 100 mg., 250 mg and 500 mg containing capsules.

| Example 1b dl-Methionine 100 mg, 250 mg or 500 mg | |
|---|---|
| dl-Methionine | 500 g |
| Lactose USP, Anhydrous q.s. or | 200 g |
| Sterotex Powder HM | 5 g |

Mix and fill as per Example 1a.

EXAMPLE 2

| TABLETS | |
|---|---|
| The Methionine Compound | 250 g |
| Corn Starch NF | 200.0 g |
| Cellulose, Microcrystalline | 46.0 g |
| Sterotex Powder HM | 4.0 g |
| Purified Water q.s. or | 300.0 ml |

Combine the corn starch, the cellulose and the methionine compound together in a planetary mixer and mix for two minutes. Add the water to this combination and mix for one minute. The resulting mix is spread on trays and dried in a hot air oven at 50 degrees C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 100 mg, 500 mg and 1000 mg respectively, of the total mix are formed with appropriate sized punches for the 50 mg, 250 mg or 500 mg containing tablets.

A preferred formulation is one where the total mix is constituted to also contain (1) at least one dietary antioxidant, preferably one or more of vitamins A, C and E, beta carotene, selenium, zinc and glutathione, each in its RDA per tablet, (2) betaine, glycine and serine each from 1/10 to 10 times the Met content per tablet, and/or (3) vitamin B12, vitamin B6 and folic acid each from 0.2 to 10 times its RDA per tablet.

EXAMPLE 3

Preparation of Intravenous Formulations

A solution 25 g of dl-Methionine is prepared in 1 liter of water for injection at room temperature with stirring. The solution is sterile filtered into 500 5-ml vials, each of which contains 2 ml of solution containing 50 mg of compound, and sealed under nitrogen.

Alternatively, after sterile filtration into vials, the water may be removed by lyophilization, and the vials then sealed aseptically, to provide a powder which is redissolved prior to injection.

Having thus described our invention, what we claim and desire by Letters Patent to secure are the following:

We claim:

1. A method for ameliorating inflammatory symptoms of respiratory disease including but not limited to edema, adult respiratory distress syndrome, asbestosis, and asthma in a subject in need of such treatment, comprising administering to the subject an antioxidant in unit dosage form comprising active components consisting essentially of an antiinflammatory amount of at least one methionine compound selected from the group consisting of the methionine hydroxy analog, and methionine compounds having the structural formula I

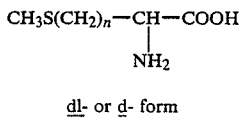

$$CH_3S(CH_2)_n-CH-COOH \quad\quad I$$
$$| $$
$$NH_2$$

dl- or d- form and pharmaceutically acceptable N- (mono- and dicarboxylic acid) acyl derivatives and alkyl esters thereof, where n is an integer from 1 to 3, and an amount of a dietary antioxidant selected from the group consisting of vitamins A, C, and E, beta carotene, selenium, zinc and glutathionine and combinations thereof where such combination becomes therapeutically effective.

2. A method for inhibiting inflammatory response in a subject according to claim 1 where the methionine compound is administered in a daily dosage in the range from 10 to 100 mg/kg of body weight until the inflammation is relieved.

3. A method according to claim 1 where the methionine compound is in the dl-form.

4. A method according to claim 1 where the methionine compound is in the d-form.

5. A method according to claim 1 where the methionine compound is administered in a daily dosage with at least one homocysteine affecting compound selected from the group consisting of betaine, glycine, serine, vitamin B12, vitamin B6, and folate, the homocysteine affecting compound being administered in an amount sufficient to enable the systemic conversion of excess homocysteine present in the system to methionine, in the case of betaine, and cysteine in the case of other homocysteine affecting compounds.

6. A method according to claim 5 where the dosage of the betaine, glycine and/or serine is from 0.1 to 10 times the dosage amount of the methionine compound.

7. A method according to claim 5 where betaine is administered in a dosage equal in amount to that of the methionine compound.

8. A method according to claim 5 where the dosage of the vitamin B12, vitamin B6 or folate corresponds to a recommended daily allowance thereof.

9. A method for ameliorating the symptom which is impaired lung function resulting from inflammation in a subject in need of such treatment according to claim 1 where the methionine compound is administered in an amount of at least 2 grams per day per 70 kg body weight for at least 5 days.

10. A method for ameliorating the symptom which is increased cough frequency in a subject in need of such treatment according to claim 1 where the methionine compound is administered in a sufficient dosage and for a time sufficient to decrease said frequency.

* * * * *